US010059749B2

United States Patent
Lin et al.

(10) Patent No.: US 10,059,749 B2
(45) Date of Patent: *Aug. 28, 2018

(54) **COMPOSITION FOR PREVENTING *MYCOPLASMA* SPP. INFECTION**

(71) Applicant: AGRICULTURAL TECHNOLOGY RESEARCH INSTITUTE, Hsinchu (TW)

(72) Inventors: Jiunn-Horng Lin, Hsinchu (TW); Jyh-Perng Wang, Hsinchu (TW); Zeng-Weng Chen, Hsinchu (TW); Chien-Yu Fang, Hsinchu (TW); Ming-Wei Hsieh, Hsinchu (TW); Ping-Cheng Yang, Hsinchu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/920,924

(22) Filed: Mar. 14, 2018

(65) Prior Publication Data

US 2018/0208629 A1 Jul. 26, 2018

Related U.S. Application Data

(62) Division of application No. 15/032,758, filed as application No. PCT/CN2013/087599 on Nov. 21, 2013, now Pat. No. 9,951,109.

(51) Int. Cl.
| | |
|---|---|
| *C07K 14/30* | (2006.01) |
| *C12N 15/70* | (2006.01) |
| *A61K 38/16* | (2006.01) |
| *A61K 39/02* | (2006.01) |

(52) U.S. Cl.
CPC ............ *C07K 14/30* (2013.01); *A61K 38/164* (2013.01); *A61K 39/02* (2013.01); *C12N 15/70* (2013.01)

(58) Field of Classification Search
None
See application file for complete search history.

(56) References Cited

U.S. PATENT DOCUMENTS

| 9,951,109 B2 * | 4/2018 | Lin .................. C07K 14/30 |
| 2003/0064079 A1 | 4/2003 | Goudie et al. |
| 2003/0109473 A1 | 6/2003 | Keich et al. |
| 2006/0233823 A1 | 10/2006 | King et al. |

FOREIGN PATENT DOCUMENTS

| CN | 1296953 A | 5/2001 |
| CN | 1612749 A | 5/2005 |
| CN | 102872456 A | 1/2013 |

OTHER PUBLICATIONS

Elongation factor Tu, UniProtKB/Swiss-Prot: Q4A9G1.1; entered May 20, 2008; pp. 1-7.
International Search Report (PCT/ISA/210) issued in PCT/CN2013/087599, dated Aug. 27, 2014.
Petrovsky et al., "Vaccine adjuvants: Current state and future trends", Immunology and Cell Biology, 2004, 488-496.
Ribonucleoside-diphosphate reductase beta chain, UniProtKB/Swiss-Prot: Q601P5; p. 1-2.
Sivori et al., p46, a Novel Natural Killer Cell-specific Surface Molecule That Mediates Cell Activation, J. Exp. Med, 1997, 1129-1136.
Sosio et al., An elongation factor Tu (EF-Tu) resistant to the EF-Tu inhibitor GE2270 in the producing organism Planobiospora rosea, Mol Microbiol., 1996, 43-51.

* cited by examiner

*Primary Examiner* — Lianko G Garyu
(74) *Attorney, Agent, or Firm* — Birch, Stewart, Kolasch & Birch, LLP (57) ABSTRACT

The present invention provides proteins that are suitable to be used as the active ingredient in subunit vaccine against *Mycoplasma* spp. The present invention also provides a subunit vaccine made therefrom. Said proteins have been experimentally proved to have the capability of inducing sufficient immune response to avoid pigs from *Mycoplasma* spp. infection. Said vaccine may have one of said proteins as active ingredient; or may have two or more of said proteins and is formulated as a cocktail vaccine. The present vaccine not only is safer than the conventional vaccines but also has equal or even better immune efficiency than the conventional ones. Furthermore, fusion partners suitable for producing said proteins of high solubility are also proved, which can significantly reduce production cost.

6 Claims, 3 Drawing Sheets

Specification includes a Sequence Listing.

SEQUENCE LISTING

```
<160> NUMBER OF SEQ ID NOS: 22

<210> SEQ ID NO 1
<211> LENGTH: 419
<212> TYPE: PRT
<213> ORGANISM: Mycoplasma hyopneumoniae

<400> SEQUENCE: 1

Met Lys Lys Met Leu Arg Lys Lys Phe Leu Tyr Ser Ser Ala Ile Tyr
1               5                   10                  15

Ala Thr Ser Leu Ala Ser Ile Ile Ala Phe Val Ala Ala Gly Cys Gly
            20                  25                  30

Gln Thr Glu Ser Gly Ser Thr Ser Asp Ser Lys Pro Gln Ala Glu Thr
        35                  40                  45

Leu Lys His Lys Val Ser Asn Asp Ser Ile Arg Ile Ala Leu Thr Asp
    50                  55                  60

Pro Asp Asn Pro Arg Trp Ile Ser Ala Gln Arg Asp Ile Ile Ser Tyr
65                  70                  75                  80

Val Asp Glu Thr Glu Ala Ala Thr Ser Thr Ile Thr Lys Asn Gln Asp
                85                  90                  95

Ala Gln Asn Asn Trp Leu Thr Gln Gln Ala Asn Leu Ser Pro Ala Pro
            100                 105                 110

Lys Gly Phe Ile Ile Ala Pro Glu Asn Gly Ser Gly Val Gly Thr Ala
        115                 120                 125

Val Asn Thr Ile Ala Asp Lys Gly Ile Pro Ile Val Ala Tyr Asp Arg
    130                 135                 140

Leu Ile Thr Gly Ser Asp Lys Tyr Asp Trp Tyr Val Ser Phe Asp Asn
145                 150                 155                 160

Glu Lys Val Gly Glu Leu Gln Gly Leu Ser Leu Ala Ala Gly Leu Leu
                165                 170                 175

Gly Lys Glu Asp Gly Ala Phe Asp Ser Ile Asp Gln Met Asn Glu Tyr
            180                 185                 190

Leu Lys Ser His Met Pro Gln Glu Thr Ile Ser Phe Tyr Thr Ile Ala
        195                 200                 205

Gly Ser Gln Asp Asp Asn Asn Ser Gln Tyr Phe Tyr Asn Gly Ala Met
    210                 215                 220

Lys Val Leu Lys Glu Leu Met Lys Asn Ser Gln Asn Lys Ile Ile Asp
225                 230                 235                 240

Leu Ser Pro Glu Gly Glu Asn Ala Val Tyr Val Pro Gly Trp Asn Tyr
                245                 250                 255

Gly Thr Ala Gly Gln Arg Ile Gln Ser Phe Leu Thr Ile Asn Lys Asp
            260                 265                 270
```

Pro Ala Gly Gly Asn Lys Ile Lys Ala Val Gly Ser Lys Pro Ala Ser
            275                 280                 285

Ile Phe Lys Gly Phe Leu Ala Pro Asn Asp Gly Met Ala Glu Gln Ala
290                 295                 300

Ile Thr Lys Leu Lys Leu Glu Gly Phe Asp Thr Gln Lys Ile Phe Val
305                 310                 315                 320

Thr Gly Gln Asp Tyr Asn Asp Lys Ala Lys Thr Phe Ile Lys Asp Gly
            325                 330                 335

Asp Gln Asn Met Thr Ile Tyr Lys Pro Asp Lys Val Leu Gly Lys Val
            340                 345                 350

Ala Val Glu Val Leu Arg Val Leu Ile Ala Lys Asn Lys Ala Ser
            355                 360                 365

Arg Ser Glu Val Glu Asn Glu Leu Lys Ala Lys Leu Pro Asn Ile Ser
370                 375                 380

Phe Lys Tyr Asp Asn Gln Thr Tyr Lys Val Gln Asp Lys Asn Ile Asn
385                 390                 395                 400

Thr Ile Leu Val Ser Pro Val Ile Val Thr Lys Ala Asn Val Asp Asn
            405                 410                 415

Pro Asp Ala

<210> SEQ ID NO 2
<211> LENGTH: 402
<212> TYPE: PRT
<213> ORGANISM: Mycoplasma hyopneumoniae

<400> SEQUENCE: 2

Met Ala Val Val Lys Thr Thr Gly Lys Lys Asp Phe Asp Arg Ser Lys
1               5 10 15

Glu His Ile Asn Ile Gly Thr Ile Gly His Val Asp His Gly Lys Thr
20 25 30

Thr Leu Thr Ala Ala Ile Ser Thr Val Leu Ala Lys Arg Gly Leu Ala
35 40 45

Glu Ala Lys Asp Tyr Ala Ser Ile Asp Ala Ala Pro Glu Glu Lys Ala
50 55 60

Arg Gly Ile Thr Ile Asn Thr Ala His Ile Glu Tyr Ser Thr Asp Lys
65 70 75 80

Arg His Tyr Ala His Val Asp Cys Pro Gly His Ala Asp Tyr Ile Lys
85 90 95

Asn Met Ile Thr Gly Ala Ala Gln Met Asp Gly Ala Ile Leu Val Val
100 105 110

Ala Ala Thr Asp Gly Pro Met Pro Gln Thr Arg Glu His Ile Leu Leu
115 120 125

Ser Lys Gln Val Gly Val Pro Lys Met Val Val Phe Leu Asn Lys Ile
130 135 140

Asp Leu Leu Glu Gly Glu Glu Glu Met Val Asp Leu Val Glu Val Glu
145 150 155 160

Ile Arg Glu Leu Leu Ser Ser Tyr Asp Phe Asp Gly Asp Asn Thr Pro
165 170 175

Ile Ile Arg Gly Ser Ala Arg Gly Ala Leu Glu Gly Lys Pro Glu Trp
180 185 190

Glu Ala Lys Val Leu Glu Leu Met Asp Ala Val Asp Ser Tyr Ile Asp
195 200 205

Ser Pro Val Arg Glu Met Asp Lys Pro Phe Leu Met Ala Val Glu Asp
210 215 220

```
Val Phe Thr Ile Thr Gly Arg Gly Thr Val Ala Thr Gly Lys Val Glu
225                 230                 235                 240

Arg Gly Gln Val Lys Leu Asn Glu Glu Val Glu Ile Val Gly Tyr Arg
            245                 250                 255

Glu Glu Pro Lys Lys Thr Val Ile Thr Gly Ile Glu Met Phe Asn Lys
        260                 265                 270

Asn Leu Gln Thr Ala Met Ala Gly Asp Asn Ala Gly Val Leu Leu Arg
    275                 280                 285

Gly Val Asp Arg Lys Asp Ile Glu Arg Gly Gln Val Ile Ala Lys Pro
290                 295                 300

Lys Thr Ile Ile Pro His Thr Lys Phe Lys Ala Ala Ile Tyr Ala Leu
305                 310                 315                 320

Lys Lys Glu Glu Gly Gly Arg His Thr Pro Phe Phe Lys Asn Tyr Lys
            325                 330                 335

Pro Gln Phe Tyr Phe Arg Thr Thr Asp Val Thr Gly Gly Ile Glu Phe
        340                 345                 350

Glu Pro Gly Arg Glu Met Val Ile Pro Gly Asp Asn Val Asp Leu Thr
    355                 360                 365

Val Glu Leu Ile Ala Pro Ile Ala Val Glu Gln Gly Thr Lys Phe Ser
370                 375                 380

Ile Arg Glu Gly Gly Arg Thr Val Gly Ala Gly Thr Val Thr Glu Ile
385                 390                 395                 400

Ile Lys

<210> SEQ ID NO 3
<211> LENGTH: 282
<212> TYPE: PRT
<213> ORGANISM: Mycoplasma hyopneumoniae

<400> SEQUENCE: 3

Ala Lys Leu Asp Asp Asn Leu Gln Tyr Ser Phe Glu Ala Ile Lys Lys
1               5                   10                  15

Gly Glu Thr Thr Lys Glu Gly Lys Arg Glu Glu Val Asp Lys Lys Val
            20                  25                  30

Lys Glu Leu Asp Asn Lys Ile Lys Gly Ile Leu Pro Gln Pro Pro Ala
        35                  40                  45

Ala Lys Pro Glu Ala Ala Lys Pro Val Ala Ala Lys Pro Glu Ala Ala
    50                  55                  60

Lys Pro Val Ala Ala Lys Pro Glu Ala Ala Lys Pro Val Ala Ala Lys
65                  70                  75                  80

Pro Glu Ala Ala Lys Pro Val Ala Ala Lys Pro Glu Ala Ala Lys Pro
            85                  90                  95

Val Ala Ala Lys Pro Glu Ala Ala Lys Pro Val Ala Ala Lys Pro Glu
        100                 105                 110

Ala Ala Lys Pro Val Ala Thr Asn Thr Gly Phe Ser Leu Thr Asn Lys
    115                 120                 125

Pro Lys Glu Asp Tyr Phe Pro Met Ala Phe Ser Tyr Lys Leu Glu Tyr
130                 135                 140

Thr Asp Glu Asn Lys Leu Ser Pro Lys Thr Pro Glu Ile Asn Val Phe
145                 150                 155                 160

Leu Glu Leu Val His Gln Ser Glu Tyr Glu Glu Lys Ile Ile Lys
            165                 170                 175

Glu Leu Asp Lys Thr Val Leu Asn Leu Gln Tyr Gln Phe Gln Glu Val
        180                 185                 190
```

```
Lys Val Ala Ser Asp Gln Tyr Gln Lys Leu Ser His Pro Met Met Thr
            195                 200                 205

Glu Gly Ser Ser Asn Gln Gly Lys Lys Ala Glu Gly Ala Pro Asn Gln
        210                 215                 220

Gly Lys Lys Ala Glu Gly Ala Pro Asn Gln Gly Lys Lys Ala Glu Gly
225                 230                 235                 240

Ala Pro Ser Gln Gly Lys Lys Ala Glu Gly Thr Ser Asn Gln Gln Ser
                245                 250                 255

Pro Thr Thr Glu Leu Thr Asn Tyr Leu Pro Asp Leu Gly Lys Lys Ile
            260                 265                 270

Asp Glu Ile Ile Lys Lys Gln Gly Lys Asn
            275                 280

<210> SEQ ID NO 4
<211> LENGTH: 96
<212> TYPE: PRT
<213> ORGANISM: Mycoplasma hyopneumoniae

<400> SEQUENCE: 4

Asp Leu Leu Tyr Lys Leu Ile Glu Leu Glu Lys Asp Tyr Leu Tyr Asp
1               5                   10                  15

Leu Tyr Ser Glu Val Gly Leu Ala Glu Ser Ala Ile Lys Phe Ser Ile
            20                  25                  30

Tyr Asn Ala Gly Lys Phe Leu Gln Asn Leu Gly Tyr Asp Ser Pro Phe
        35                  40                  45

Ser Lys Glu Glu Thr Glu Ile Glu Pro Glu Ile Phe Ser Gln Leu Ser
    50                  55                  60

Ala Arg Ala Asp Glu Asn His Asp Phe Phe Ser Gly Asn Gly Ser Ser
65                  70                  75                  80

Tyr Val Met Ala Leu Ala Glu Glu Thr Glu Asp Glu Asp Trp Glu Phe
                85                  90                  95

<210> SEQ ID NO 5
<211> LENGTH: 1260
<212> TYPE: DNA
<213> ORGANISM: Mycoplasma hyopneumoniae

<400> SEQUENCE: 5
atgaaaaaaa tgcttagaaa aaaattcttg tattcatcag ctatttatgc aacttcgctt      60
gcatcaatta ttgcatttgt tgcagcaggt tgtggacaga cagaatcagg ttcgacttca     120
gattctaaac cacaagccga gactctaaaa cataaagtaa gtaatgattc tattcgaata     180
gcactaaccg atccggataa tcctcgatga attagtgccc aaagagatat tatttcttat     240
gttgatgaaa cagaggcagc aacttcaaca attacaaaaa accaggatgc acaaaataac     300
tgactcactc agcaagctaa tttaagtcca gcgccaaaag gatttattat tgcccctgaa     360
aatggaagtg gagttggaac tgctgttaat acaattgctg ataaaggaat tccgattgtt     420
gcctatgatc gactaattac tggatctgat aaatatgatt ggtatgtttc ttttgataat     480
gaaaaagttg gtgaattaca aggtctttca cttgctgcgg gtctattagg aaaggaagat     540
ggtgcttttg attcaattga tcaaatgaat gaatatctaa aatcacatat gccccaagag     600
acaatttctt tttatacaat cgcgggttcc caagatgata ataactccca atatttttat     660
aatggtgcaa tgaaagtact taaagaatta atgaaaaatt cgcaaaataa aataattgat     720
ttatctcctg aaggcgaaaa tgctgtttat gtcccaggat gaaattatgg aactgccggt     780
caaagaatcc aatcttttct aacaattaac aaagatccag caggtggtaa taaaatcaaa     840
```

```
gctgttggtt caaaaccagc ttctattttc aaaggatttc ttgccccaaa tgatggaatg      900
gccgaacaag caatcaccaa attaaaactt gaaggatttg atacccaaaa aatctttgta      960
actggtcaag attataatga taaagccaaa acttttatca agacggcga tcaaaatatg     1020 acaatttata aacctgataa agttttagga aaagttgctg ttgaagttct tcgggtttta     1080
attgcaaaga aaataaagc atctagatca gaagtcgaaa acgaactaaa agcaaagcta     1140
ccaaatattt catttaaata tgataatcaa acatataaag tacaagataa aaatattaat     1200
acaattttag taagtccagt aattgttaca aaagctaatg ttgataatcc tgatgcctaa     1260
```

<210> SEQ ID NO 6
<211> LENGTH: 1209
<212> TYPE: DNA
<213> ORGANISM: Mycoplasma hyopneumoniae

<400> SEQUENCE: 6

```
atggcagttg ttaaaacgac aggaaaaaaa gactttgatc gttccaaaga acatattaat     60
attggaacaa ttggtcatgt tgaccatgga aaaacaacac taacagcagc aatttcaact    120
gttttggcaa aaagaggact cgcggaggca aaggattatg cctcaattga tgcagctcct    180
gaagaaaaag cacgaggaat tacaattaat accgcccata ttgaatatag cactgacaaa    240
cggcactatg cccatgttga ttgcccaggt catgccgatt atataaaaaa tatgatcacc    300
ggagcggccc aaatggatgg agcaatttta gtggttgcag caaccgatgg cccaatgcct    360
caaactcgtg aacacatttt attatcaaaa caagttggtg tcccaaaaat ggttgttttc    420
cttaataaaa ttgacttact tgaaggcgaa gaagaaatgg ttgatttagt tgaggtcgaa    480
attcgcgaac ttctttcttc ttatgatttt gatggcgata atactccaat tattcgggga    540
tctgctcgtg ggcccttga aggaaaacct gaatgggagg caaaagtact tgaattgatg    600
gacgcagttg attcttatat tgactcacct gttcgggaaa tggataaacc ctttttgatg    660
gccgttgagg atgtttttac aattacagga cgtggaaccg tagcaacggg aaaagttgaa    720
agaggtcaag ttaaactaaa cgaagaagtg gaaattgtgg gttatcgcga agaacctaaa    780
aagaccgtaa tcaccggaat tgaaatgttt aataaaaatc ttcaaactgc gatggctggg    840
gataatgccg gtgttctcct acgtggagta gatcgaaaag atatcgaacg tggtcaggtt    900
attgcaaaac caaaaacaat tataccgcat acaaaattta aagctgcaat ttatgccctt    960
aaaaaagaag aaggcggaag gcatacacca tttttcaaaa attataaacc acaattttat   1020
tttcgaacta ccgatgtaac aggcggaatc gagtttgaac caggtcgcga gatggtaatt   1080
ccgggggata atgttgatct taccgttgaa ttaattgccc caattgccgt tgagcaggga   1140
accaaattct cgatccgaga aggtggtaga accgtgggtg ccggaacagt taccgaaatt   1200
attaaataa                                                           1209
```

<210> SEQ ID NO 7
<211> LENGTH: 849
<212> TYPE: DNA
<213> ORGANISM: Mycoplasma hyopneumoniae

<400> SEQUENCE: 7

```
gcaaaattag acgataatct tcagtattca tttgaagcta tcaaaaaagg ggaaactaca     60
aaagaaggta aaagagaaga agtagataaa aaagttaagg aattagataa taaaataaaa    120
ggtatattgc ctcagccccc agcggctaaa ccagaagcag caaaaccagt agcggctaaa    180
```

```
ccagaagcag caaaaccagt agcggctaaa cctgaagcag caaaaccagt agcggctaaa      240
cctgaagcag caaaaccagt tgcggctaaa cctgaagcag caaaaccagt tgcggctaaa      300
cctgaagcag caaaaccagt tgcagctaaa cctgaagcag caaaaccagt tgctactaat      360
actggctttt cacttacaaa taaaccaaaa gaagactatt tcccaatggc ttttagttat      420
aaattagaat atactgacga aaataaatta agcccaaaaa caccggaaat taatgtatttt     480 ttagaactag ttcatcaaag cgagtatgaa gaacaaaaaa taataaagga actagacaaa      540
actgttttaa atcttcaata tcaattccag gaagtcaagg tagctagtga tcaatatcag      600
aaacttagcc acccaatgat gaccgaggga tcttcaaatc aaggtaaaaa agcagaggga      660
gctcctaacc aagggaaaaa agcagaggga gctcctaacc aagggaaaaa agcagagggc      720
gctcctagtc aaggaaaaaa agccgaagga acttctaacc aacaaagccc aactaccgaa      780
ttaactaatt accttcctga cttaggtaaa aaaattgacg aaatcattaa aaaacaaggt      840
aaaaattaa                                                              849

<210> SEQ ID NO 8
<211> LENGTH: 291
<212> TYPE: DNA
<213> ORGANISM: Mycoplasma hyopneumoniae

<400> SEQUENCE

<210> SEQ ID NO 12
<211> LENGTH: 39
<212> TYPE: DNA
<213> ORGANISM: Artificial Sequence
<220> FEATURE:
<223> OTHER INFORMATION: PRIMER

<400> SEQUENCE: 12
caatatgtcg acttaggcat caggattatc aacattagc					39

<210> SEQ ID NO 13
<211> LENGTH: 52
<212> TYPE: DNA
<213> ORGANISM: Artificial Sequence
<220> FEATURE:
<223> OTHER INFORMATION: PRIMER

<400> SEQUENCE: 13
gatataggat ccgatctatt atataaacta attgaattag aaaaagatta tc					52

<210> SEQ ID NO 14
<211> LENGTH: 37
<212> TYPE: DNA
<213> ORGANISM: Artificial Sequence
<220> FEATURE:
<223> OTHER INFORMATION: PRIMER

<400> SEQUENCE: 14
caatatgtcg acttaaaact cccaatcttc atcttcg					37

<210> SEQ ID NO 15
<211> LENGTH: 39
<212> TYPE: DNA
<213> ORGANISM: Artificial Sequence
<220> FEATURE:
<223> OTHER INFORMATION: PRIMER

<400> SEQUENCE: 15
gatataggat ccatggcagt tgttaaaacg acaggaaaa					39

<210> SEQ ID NO 16
<211> LENGTH: 43
<212> TYPE: DNA
<213> ORGANISM: Artificial Sequence
<220> FEATURE:
<223> OTHER INFORMATION: PRIMER

<400> SEQUENCE: 16
caatatgtcg acttatttaa taatttcggt aactgttccg gca					43

<210> SEQ ID NO 17
<211> LENGTH: 34
<212> TYPE: DNA
<213> ORGANISM: Artificial Sequence
<220> FEATURE:
<223> OTHER INFORMATION: PRIMER

<400> SEQUENCE: 17
ctctttgggc actaatccat cgaggattat ccgg					34

<210> SEQ ID NO 18
<211> LENGTH: 34
<212> TYPE: DNA
<213> ORGANISM: Artificial Sequence
<220> FEATURE:
<223> OTHER INFORMATION: PRIMER

```
<400> SEQUENCE: 18
ccggataatc ctcgatggat tagtgcccaa agag                              34

<210> SEQ ID NO 19
<211> LENGTH: 37
<212> TYPE: DNA
<213> ORGANISM: Artificial Sequence
<220> FEATURE:
<223> OTHER INFORMATION: PRIMER

<400> SEQUENCE: 19
attagcttgc tgagtgagcc agttattttg tgcatcc                           37

<210> SEQ ID NO 20
<211> LENGTH: 37
<212> TYPE: DNA
<213> ORGANISM: Artificial Sequence
<220> FEATURE:
<223> OTHER INFORMATION: PRIMER

<400> SEQUENCE: 20
ggatgcacaa ataactggc tcactcagca agctaat                            37

<210> SEQ ID NO 21
<211> LENGTH: 34
<212> TYPE: DNA
<213> ORGANISM: Artificial Sequence
<220> FEATURE:
<223> OTHER INFORMATION: PRIMER

<400> SEQUENCE: 21
cggcagttcc ataattccat cctgggacat aaac                              34

<210> SEQ ID NO 22
<211> LENGTH: 34
<212> TYPE: DNA
<213> ORGANISM: Artificial Sequence
<220> FEATURE:
<223> OTHER INFORMATION: PRIMER

<400> SEQUENCE: 22
gtttatgtcc caggatggaa ttatggaact gccg                              34
```

COMPOSITION FOR PREVENTING *MYCOPLASMA* SPP. INFECTION

CROSS-REFERENCE TO RELATED APPLICATIONS

This application is a Divisional of copending U.S. application Ser. No. 15/032,758, filed on Apr. 28, 2016, which is the National Phase under 35 U.S.C. § 371 of International Application No. PCT/CN2013/087599, filed on Nov. 21, 2013, all of which are hereby expressly incorporated by reference into the present application.

BACKGROUND

Technical Field

The present disclosure relates to a vaccine against *Mycoplasma* spp.; especially to a subunit vaccine against *Mycoplasma* spp.

Description of Related Art

*Mycoplasma* spp. is currently known the tiniest bacteria capable of self-replication outside host cells. Although swine enzootic pneumonia would not cause swine death, it will reduce feeding efficiency and cause growth retardation, inflammation, and immunosuppression as well as make swine more vulnerable to infection of other pathogens, which therefore become economic damage of the industry.

So far, swine enzootic pneumonia is prevented by three major strategies, including: medicine administration, environment management, and vaccination. Seeing the bad prevention efficiency of antibiotics to *Mycoplasma hyopneumoniae*, medicine administration can only used for treatment purposes and is hard to meet prevention needs. Furthermore, considering that drug abuse may lead to a larger infection causing by drug-resistant bacteria, medicine administration needs cautious plans and exists a lot of limitations.

Environment management forms the basis of prevention of *Mycoplasma* spp. infection. Good piggery sanitation and management would be helpful to reduce occurrence of infection. On the other hand, prevention could be more comprehensive through vaccination.

The conventional vaccines in the field use inactive/dead bacteria as the active ingredient thereof. However, the price of the conventional vaccines is too high because *Mycoplasma* spp. is fastidious bacteria and is to difficult to be cultured in the laboratory. In order to reduce the cost of *Mycoplasma* spp. vaccines, scientists continuously try to develop vaccines of different types, such as: (1) attenuated vaccines, (2) vector vaccines, (3) subunit vaccines, and (4) DNA vaccines. Among them, subunit vaccines show the most potential because the advantages of ease in production and high safety.

To date, there are several potential candidate proteins that could be used for *M. hyopneumoniae* vaccines; however, there is no further report verifying the proteins suitable for *M. hyopneumoniae* vaccines.

SUMMARY

In light of the foregoing, one of the objects of the present invention is to provide antigens suitable for being used in *Mycoplasma* spp. vaccines and thereby producing novel *Mycoplasma* spp. vaccines so that the cost of prevention can be reduced.

Another object of the present invention is to provide a combination of antigens that suitable for being used in *Mycoplasma* spp. vaccines and thereby provide subunit vaccines with better performance; therefore, there would be more options for prevention tasks.

In order to achieve the aforesaid objects, the present invention provides a protein for preventing *Mycoplasma* spp. infection, comprising an amino acid sequence of SEQ ID NO: 01, SEQ ID NO: 02, or a combination thereof.

The present invention also provides a composition for preventing *Mycoplasma* spp. infection, comprising: a first active ingredient, comprising a protein of P46, Tuf, or a combination thereof; and a pharmaceutically acceptable adjuvant.

Preferably, said first active ingredient has an amino acid sequence of SEQ ID NO: 01, SEQ ID NO: 02, or a combination thereof.

Preferably, said composition further comprises a second active ingredient, comprising a protein of MHP30, NrdFC, or a combination thereof.

Preferably, said second active ingredient has an amino acid sequence of SEQ ID NO: 03, SEQ ID NO: 04, or a combination thereof.

Preferably, said first active ingredient and/or said second active ingredient is independently of a concentration of 20 to 2000 µg/mL based on the total volume of said composition.

Preferably, said pharmaceutically acceptable adjuvant is a complete Freund's adjuvant, an incomplete Freund's adjuvant, an alumina gel, a surfactant, a polyanion adjuvant, a peptide, an oil emulsion, or a combination thereof.

Preferably, said composition further comprises a pharmaceutically acceptable additive.

Preferably, said pharmaceutically acceptable additive is a solvent, a stabilizer, a diluent, a preservative, an antibacterial agent, an antifungal agent, an isotonic agent, an absorption delaying agent, or a combination thereof.

The present invention further provides a composition for preventing *Mycoplasma* spp. infection, comprising: an active ingredient, having at least two proteins selected from a group consisting of P46, Tuf, MHP30, and NrdFC; and a pharmaceutically acceptable adjuvant.

Preferably, said active ingredient is P46, Tuf, MHP30, and NrdFC.

Preferably, said active ingredient has at least two amino acid sequences selected form a group consisting of SEQ ID NO: 01, SEQ ID NO: 02, SEQ ID NO: 03, and SEQ ID NO: 04.

Preferably, said active ingredient has amino acid sequences of SEQ ID NO: 01, SEQ ID NO: 02, SEQ ID NO: 03, and SEQ ID NO: 04.

Preferably, said active ingredient is of a concentration of 20 to 2000 µg/mL based on the total volume of said composition.

Preferably, said pharmaceutically acceptable adjuvant is a complete Freund's adjuvant, an incomplete Freund's adjuvant, an alumina gel, a surfactant, a polyanion adjuvant, a peptide, an oil emulsion, or a combination thereof.

Preferably, said composition further comprises a pharmaceutically acceptable additive.

Preferably, said pharmaceutically acceptable additive is a solvent, a stabilizer, a diluent, a preservative, an antibacterial agent, an antifungal agent, an isotonic agent, an absorption delaying agent, or a combination thereof.

The present invention also provides an expression vector for preparing the aforesaid active ingredient; wherein said expression vector comprises a plasmid; wherein said plasmid comprises: a nucleotide sequence comprising at least one sequence selected from a group consisting of SEQ ID NO: 05, SEQ ID NO: 06, SEQ ID NO: 07, and SEQ ID NO: 08; a gene encoding a fusion partner, selected from a group consisting of MsyB of *E. coli*, YjgD of *E. coli*, GroS17 of *E. coli*, GroES of *Bacillus subtilis*, TrxA of *Alicyclobacillus acidocaldarius*, SUMO of *S. cerevisiae*, and Vgb of *Vitreoscilla* spp.; and a regulatory element.

Preferably, said regulatory element comprises a promoter and a ribosome binding site.

Preferably, said plasmid is pET-MSY, pET-YjgD, pET-GroS17, pET-GroES, pET-TrxA, pET-SUMO, or pET-Vgb.

Preferably, regarding said expression vector, provided that, when said nucleotide sequence is at least one sequence selected from a group consisting of SEQ ID NO: 05, SEQ ID NO: 06, and SEQ ID NO: 08, said gene encoding a fusion partner is MsyB of *E. coli*.

Preferably, regarding said expression vector, provided that, when said nucleotide sequence is SEQ ID NO: 07, said gene encoding a fusion partner is selected from a group consisting of YjgD of *E. coli*, GroS17 of *E. coli*, GroES of *Bacillus subtilis*, TrxA of *Alicyclobacillus acidocaldarius*, SUMO of *S. cerevisiae*, and Vgb of *Vitreoscilla* spp.

Preferably, said expression vector is applied for used for an *E. coli* gene expression system.

The present invention further provides a method for preparing soluble antigen, comprising using the aforesaid expression vector; wherein said antigen is P46, Tuf, MHP30, or NrdFC.

To sum up, the present invention is related to antigens, composition, and expression vector for preparing said antigen for preventing from *Mycoplasma* spp. infection. The present disclosure not only provides new options for prevention tasks, but also proves that a "cocktail" subunit vaccine of combining at least two antigens (that is, having at least two antigens as active ingredients) is able to enhance the immune induction. Moreover, the present invention teaches some fusion partners that are particularly suitable for assisting the expression of the aforesaid antigens in an expression system so that are favorable for increasing the production capacity of preparing the required vaccines.

BRIEF DESCRIPTION OF THE DRAWINGS

FIG. 1 is a result of a protein electrophoresis, showing various fusion partners have different effects on the solubility of MHP 30 prepared. Line M: protein marker (PageRuler™ pretained protein ladder; Fermentas, USA); Line 1: *E. coli* BL21 (DE3) (pET-YjgD-MHP30), soluble protein; Line 2: *E. coli* BL21 (DE3) (pET-SUMO-MHP30), soluble protein; Line 3: *E. coli* BL21 (DE3) (pET-GroS17-MHP30), soluble protein; Line 4: *E. coli* BL21 (DE3) (pET-GroES-MHP30), soluble protein; Line 5: *E. coli* BL21 (DE3) (pET-D-MHP30), soluble protein; Line 6: *E. coli* BL21 (DE3) (pET-MsyB-MHP30), soluble protein; Line 7: *E. coli* BL21 (DE3) (pET-Vgb-MHP30), soluble protein; Line 8: *E. coli* BL21 (DE3) (pET-TrxA-MHP30), soluble protein.

DETAILED DESCRIPTION

The present invention is related to antigens, composition, and expression vector for preparing said antigen for preventing from *Mycoplasma* spp. infection. Specifically, the present invention proves the antigenic effect of P46 and Tuf for preparing composition for *Mycoplasma* spp. infection prevention. Furthermore, the present invention also proves a "cocktail" subunit vaccine of combining at least two of P46, Tuf, MHP30, and NrdFC as active ingredients is able to enhance the immune induction. On the other hand, the present invention discloses fusion partners, which are particularly suitable for preparing P46, Tuf, MHP30, and NrdFC of high solubility (ie. water-solubility). Through using the aforesaid fusion partners, the time and cost required for preparing vaccines can be significantly reduced.

In one aspect of the present invention, the present invention provides composition for preventing *Mycoplasma* spp. infection, comprising: a first active ingredient, comprising a protein of P46, Tuf, or a combination thereof; and a pharmaceutically acceptable adjuvant. In an alternative embodiment, said composition may further comprise a second active ingredient. Said second active ingredient comprises a protein of MHP30, NrdFC, or a combination thereof.

In another aspect of the present invention, the present invention provides a composition for preventing *Mycoplasma* spp. infection, comprising: an active ingredient, having at least two proteins selected from a group consisting of P46, Tuf, MHP30, and NrdFC; and a pharmaceutically acceptable adjuvant.

In an alternative embodiment of the present invention, said P46 is corresponding to the amino acid sequence showed as SEQ ID NO: 01; said Tuf is corresponding to the amino acid sequence showed as SEQ ID NO: 02; said MHP30 is corresponding to the amino acid sequence showed as SEQ ID NO: 03; said NrdFC is corresponding to the amino acid sequence showed as SEQ ID NO: 04. Those having ordinary skill in the art can readily understand that as long as the antigenic determinant formed by folding of a peptide of said amino acid sequence is not interfered, said active ingredient may be a fusion protein with at least two said sequences.

Typically, combining two or more antigens in one single vaccine is not always favorable for the immune induction of the vaccine. In fact, combining two or more antigens in one single vaccine may cause undesired situation that the immune induction of the two or more antigens conflict with each other and are thereby reduced. Besides, from the perspective of cost, even if not conflicting with each other, if the immune induction of the two or more antigens do not exhibit synergistic effect, it would be worthless to combine two or more antigens in one single vaccine. The researches of the present invention proved that P46, Tuf, MHP30, and NrdFC exhibited better immune induction while be used in combination. Therefore, in an alternative embodiment, said active ingredient of the present composition comprises any two or more of the aforesaid proteins; that is, the cocktail vaccine of the present invention.

The concentration of said active ingredient(s) in the present composition is 20 to 2000 μg/mL based on the total volume of said composition. In a preferable embodiment of the present invention, one active ingredient in the present composition is of a concentration of 20 to 500 μg/mL based on the total volume of said composition. In an alternative embodiment of the present invention, the present composition contains at least one of said proteins as active ingredients; wherein the total concentration of those active ingredients is 20 to 1000 μg/mL, 20 to 1500 μg/mL or 20 to 2000 μg/mL based on the total volume of said composition.

Said pharmaceutically acceptable adjuvant is used for improving the immune effect of said active ingredient, stabilizing said active ingredient, and/or increasing the safety of vaccines. Said pharmaceutically acceptable adjuvant of the present invention includes, but not limits to: a complete Freund's adjuvant, an incomplete Freund's adjuvant, an alumina gel, a surfactant, a polyanion adjuvant, a peptide, an oil emulsion, or a combination thereof.

Another aspect of the present invention is related to an expression vector. Specifically, said expression vector is used for an *E. coli* expression system. In other words, said expression vector is able to be translated into a peptide of amino acid sequence of desired protein, and the peptide can fold forming the desired active ingredient required for the present composition. However, based on the spirit of the present invention, those having ordinary skill in the art can refer to the disclosure of the present invention and make modification accordingly to fit in various expression system while still belong to the scope of the present invention (for instance, making modification to the sequences in order to correspond to different codon usage).

Another aspect of the present invention is related to a method for preparing a protein for preventing from *Mycoplasma* spp. infection by using said expression vector. Proteins prepared by the conventional expression vectors in the field usually have drawback of insolubility; therefore it is necessary to treat and solve the purified product by urea and guanidinium hydrochloride. However, those treatments not only increase production cost but also cause denature of the proteins so that re-folding is sometimes needed for those denatured proteins for regain their antigenic function. While there is certain possibility that the re-folding process may fail, the antigenic effect of those proteins might be reduced. In light of the insufficiency of the aforesaid conventional preparation, the present method has strength in matching fusion partner that is particularly suitable for providing excellent solubility to the aforesaid proteins for *Mycoplasma* spp. infection prevention. Therefore, the production cost can be saved, the preparation procedures can be simplified, and the efficacy of the produced proteins of being the active ingredients of vaccines can be enhanced.

In an alternative embodiment of the present invention, said expression vector comprises a plasmid. Said plasmid comprises: a nucleotide sequence, a gene encoding a fusion partner and a regulatory element. Said nucleotide sequence comprises at least one sequence selected from a group consisting of SEQ ID NO: 05, SEQ ID NO: 06, SEQ ID NO: 07, and SEQ ID NO: 08, which respectively correspond to P46, Tuf, MHP30, and NrdFC.

In an alternative embodiment, as long as the operation of the gene expression system is not hindered and the production of said nucleotide sequence and the folding of the consequent amino acid sequence thereof are not interfered, said plasmid may comprise two or more said nucleotide sequences.

Said gene encoding a fusion partner is selected from a group consisting of MsyB of *E. coli*, YjgD of *E. coli*, GroS17 of *E. coli*, GroES of *Bacillus subtilis*, TrxA of *Alicyclobacillus acidocaldarius*, SUMO of *S. cerevisiae*, and Vgb of *Vitreoscilla* spp.

Said regulatory element is referred to an element required for initiating the transcription and translation in the expression system. Said regulatory element shall at least comprise a promoter, and a ribosome binding site. Preferably, said regulatory element may further comprise: an operator, an enhancer sequence, or a combination thereof.

The following examples recite the trials and experiments of the present invention in order to further explain the features and advantages of the present invention. It shall be noted that the following examples are exemplary and shall not be used for limiting the claim scope of the present invention.

Example 1: Strains and Culture Thereof

Current researches identified there are seven kinds of *Mycoplasm* spp. isolated from swines: *Mycoplasm hyopneumoniae*, *Mycoplasma hyorhinis*, *Mycoplasma hyosynoviae*, *Mycoplasma flocculare*, *Mycoplasma hyopharyngis*, *Mycoplasma sualvi*, and *Mycoplasma bovigenitalium* (Gourlay et al., 1978; Blank et al., 1996; Assuncao et al., 2005). Among them, *Mycoplasm hyopneumoniae* is the main pathogen causing swine 25 *mycoplasma* pneumonia. The infection rate is somewhere in between 25% to 93%. Therefore, the present research used *Mycoplasm hyopneumoniae* (*Mycoplasm hyopneumoniae*, PRIT-5) as the source of antigen gene. In addition, the present research used *Escherichia coli* JM109 as the host for gene cloning and *Escherichia coli* BL21 (DE3) as host for protein expression.

*M. hyopneumoniae* was cultured by using Friis medium (Friis et al., 1975). *Escherichia coli* (*E. coli*) strains were cultured by using LB medium (Luria-Bertani). Proper amount of antibiotic and/or 1.5% of agar for preparing solid medium were optionally added in accordance the experiment conditions.

Example 2: Cloning of *M. hyopneumoniae* Antigen Gene

Specific primers were designed for different antigen genes (Table 1). The genome of *M. hyopneumoniae* was used as template and amplification was conducted by using the aforesaid primers. The details of gene amplification and cloning were described in the following paragraphs:

TABLE 1

Primer sets for amplifying the desired genes.

| Desired genes | Sequence of primer (5' to 3') |
|---|---|
| MHP30 | MHP30F (SEQ ID NO 09):<br>GATATA*GGATCC*GCAAAATTAGACGATAATCTTCAGTATTCA<br>MHP30R (SEQ ID NO 10):<br>CAATAT*GTCGAC*TTAATTTTTACCTTGTTTTTTAATGATTTCGTC |
| P46 | P46F (SEQ ID NO 11):<br>GATATA*GGATCC*ATGAAAAAAATGCTTAGAAAAAAATTCTTG<br>P46R (SEQ ID NO 12):<br>CAATAT*GTCGAC*TTAGGCATCAGGATTATCAACATTAGC |
| NrdFC | NrdCF (SEQ ID NO 13):<br>GATATA*GGATCC*GATCTATTATATAAACTAATTGAATTAGAAAAAGATTATC<br>NrdCR (SEQ ID NO 14):<br>CAATAT*GTCGAC*TTAAAACTCCCAATCTTCATCTTCG |
| Tuf | TufF (SEQ ID NO 15):<br>GATATA*GGATCC*ATGGCAGTTGTTAAAACGACAGGAAAA<br>TufR (SEQ ID NO 16):<br>CAATAT*GTCGAC*TTATTTAATAATTTCGGTAACTGTTCCGGCA |

*GGATCC: BamHI cutting site; GTCGAC: SalI cutting site

1. Extraction of *M. hyopneumoniae* Genome.

The extraction of *M. hyopneumoniae* genome was conducted by using DNA purification kit (Tissue & Cell Genomic DNA Purification kit; GeneMark, Taiwan). First, 4.5 mL of broth was put under centrifugation (5,870×g, 5 min) in tubes to discard the supernatant and collect the pellet. Then, 20 µL of proteinase K (10 mg/mL) and 200 µL of extraction reagent were added in for reacting at 56° C. for 3 hours. The pellet and the aforesaid reagents were mixed by up-side-down or shaking to the tube every 5 minutes during the period to make sure they were well-mixed.

After reaction with the extraction reagent, the solution became transparent as the pellet was digested completely. 200 µL of binding reagent was then added in for reacting at 70° C. for 10 minutes. After that, 200 µL of absolute ethanol was added into the tube and mixed. All the contents inside the tube were moved to a spin column and the spin column was then positioned in a collection tube. After centrifugation (17,970×g) for 2 minutes, the effluent was discarded and 700 µL of wash solution was added into the spin column. After another centrifugation (17,970×g) for 2 minutes, the effluent was discarded and the aforesaid procedure was repeated again. Lastly, the tube was put under centrifugation (17,970×g) for 5 minutes to remove residual ethanol. Then, the spin column was position in a sterile tube and a proper amount of sterile water was added in for elute the DNA.

The concentration of the purified *M. hyopneumoniae* genomic DNA was determined by using Quant-iT™ dsDNA High-Sensitivity Assay Kit (Invitrogen, Madison, USA) and Qubit Fluorometer (Invitrogen, Madison, USA). The operation is: mixing Quant-iT reagent and Quant-iT buffer at a ratio of 1:200 to obtain a working solution. 190 µL of working solution and 10 µL of the standard sample were mixed and placed in room temperature for 2 minutes. Then, a standard curve was depicted. After that, 2 µL of sample and 198 µL of working solution were mixed, placed for 2 minutes and detected by Qubit Fluorometer for determining the concentration of the genomic DNA. The calculation formula of the concentration (ng/µL) was: measured value× 100.

2. Amplification of Desired Genes by Polymerase Chain Reaction (PCR)

The *M. hyopneumoniae* genomic DNA was used as template and primers designed for P46 gene, Tuf gene, MHP30 gene, and NrdFC gene were respectively used for PCR reaction. Each primer used and conditions for the PCR reaction were shown in the following Table 2 (the sequences of the primers were listed in Table 1 above). 50 µL of PCR mixture contained 1×GDP-HiFi PCR buffer B, 200 µM of mixture of dATP, dTTP, dGTP, and dCTP, 1 µM amplification primer, 200 ng of *M. hyopneumoniae* genomic DNA and 1 U of GDP-HiFi DNA polymerase. After the PCR reaction, gel electrophoresis was conducted to confirm the existing of the amplified DNA fragment of expected size.

TABLE 2

PCR conditions and primer sets

| Desired genes | Primer set | Conditions |
|---|---|---|
| MHP30 | MHP30F<br>MHP30R | 98° C. for 5 minutes (one cycle); 94° C. for 30 seconds, 55° C. for 30 seconds, 68° C. for 30 seconds (35 cycles); 68° C. for 5 minutes (one cycle). |
| P46 | P46F<br>P46R | 98° C. for 5 minutes (one cycle); 94° C. for 30 seconds, 55° C. for 30 seconds, 68° C. for 45 seconds (35 cycles); 68° C. for 5 minutes (one cycle). |
| NrdFC | NrdCF<br>NrdCR | 98° C. for 5 minutes (one cycle); 94° C. for 30 seconds, 55° C. for 30 seconds, 68° C. for 30 seconds (35 cycles); 68° C. for 5 minutes (one cycle). |

TABLE 2-continued

PCR conditions and primer sets

| Desired genes | Primer set | Conditions |
|---|---|---|
| Tuf | TufF<br>TufR | 98° C. for 5 minutes (one cycle); 94° C. for 30 seconds, 55° C. for 30 seconds, 68° C. for 45 seconds (35 cycles); 68° C. for 5 minutes (one cycle). |

3. Collection of the PCR Product and Cloning Thereof.

The collection of the PCR products was made by using the PCR-M™ Clean Up system kit (GeneMark, Taiwan; the experiments were conducted by following the operation manual and were not reiterated here). Then, the cloning was made by using the CloneJET PCR Cloning Kit. The experiments of cloning were conducted according to the operation manual, which were briefly described as follows. Firstly, the collected PCR product was mixed with the reagents and DNA ligase of the kit for conducting ligation reaction at 22° C. for 30 minutes. The ligation mixture was then transformed into E. coli strain ECOS™ 9-5 (Yeastern, Taiwan). The conditions of transformation were referred to the manual. The bacteria transformed were transferred into 1 mL of SOC recovering medium and cultured at 37° C. with shaking at 250 rpm. A proper amount of broth was plating on LB solid medium plates with ampicillin (100 µg/mL) and the plates were cultured at 37° C. for 16 hours. After that, a colony PCR was conducted to screen the strains, whose transformation succeeded. The colony PCR was conducted as following steps. First of all, a tube containing PCR mixture of 50 µL of 2× Taq PCR MasterMix (Genomics, Taiwan), 0.5 µL of forward primer for amplifying the desired gene, 0.5 µL of reverse primer for amplifying the desired gene, and 49 µL sterile water was prepared. After mixing, the PCR mixture was distributed to several PCR tubes (10 µL/tube). Colonies on the aforesaid plates were randomly picked into the PCR tubes respectively for PCR reaction. The conditions of PCR reaction are: 95° C. for 5 minutes (one cycle); 95° C. for 30 seconds, 55° C. for 30 seconds, 72° C. for X minutes (25 cycles); 72° C. for 7 minutes (one cycle); wherein the "X" was depended on the extension time required for the DNA polymerase and was set according to the size of the fragment to be amplified. The extension rate of Taq DNA polymerase is 1 kb/min; therefore, if the fragment to be amplified has a size of about 1 kb, the "X" would be set as 1 minute. After reaction, a gel electrophoresis was conducted to confirm the PCR results. For those transformation strains being confirmed successfully had insert DNA in their recombinant plasmids, the plasmids were extracted out for DNA sequencing. The plasmids have MHP30 gene, P46 gene, NrdFC gene, and Tuf gene were respectively named as pJET-MHP30, pJET-P46, pJET-NrdFC, and pJET-Tuf.

The DNA sequencing results showed that the P46 coloned in the present invention has an amino sequence and nucleotide sequence as SEQ ID NO 01 and SEQ ID NO 05 respectively. Tuf has an amino sequence and nucleotide sequence as SEQ ID NO 02 and SEQ ID NO 06 respectively. MHP30 has an amino sequence and nucleotide sequence as SEQ ID NO 03 and SEQ ID NO 07 respectively. NrdFC has an amino sequence and nucleotide sequence as SEQ ID NO 04 and SEQ ID NO 08, respectively.

Example 3: Point Mutation and Cloning of P46 Gene

P46 has three TGA codons. TGA codon was translated as tryptophan in Mycoplasma spp. but as stop codon in E. coli.

In order to prevent from failure in using E. coli expression system for producing the whole desired protein, point mutation must be made to P46 gene's TGA codon to replace them as TGG, which is translated by E. coli as tryptophan.

The principle for designing mutation primers for the point mutation is the mutation point shall be located in the centre area of the primer and the Tm of the primers shall be higher than 78° C. The Tm of the primers can be calculated by the formula provided by Invitrogene: Tm=81.5+0.41 (% GC)−675/N−% mismatch. "% GC" stands for the percentage of G and C of the primer concerned; "N" stands for the length of the primer concerned; "% mismatch" stands for the percentage of the base to be mutated of the primer concerned. The primers used for point mutation of P46 gene were listed in the following Table 3, including P46F/P46M2, P46M1/P46M4, P46M3/P46M6 and P46M5/P46R.

TABLE 3

Primers used for point mutation of P46 gene

| Desired genes | Sequence of primer (5' to 3') |
|---|---|
| P46F | SEQ ID NO 11:<br>GATATAGGATCCATGAAAAAAATGCTTAGAAAAAAAT-<br>TCTTG |
| P46M2 | SEQ ID NO 17:<br>CTCTTTGGGCACTAATCCATCGAGGATTATCCGG |
| P46M1 | SEQ ID NO 18:<br>CCGGATAATCCTCGATGGATTAGTGCCCAAAGAG |
| P46M4 | SEQ ID NO 19:<br>ATTAGCTTGCTGAGTGAGCCAGTTATTTTGTGCATCC |
| P46M3 | SEQ ID NO 20:<br>GGATGCACAAAATAACTGGCTCACTCAGCAAGCTAAT |
| P46M6 | SEQ ID NO 21:<br>CGGCAGTTCCATAATTCCATCCTGGGACATAAAC |
| P46M5 | SEQ ID NO 22:<br>GTTTATGTCCCAGGATGGAATTATGGAACTGCCG |
| P46R | SEQ ID NO 12:<br>CAATATGTCGACTTAGGCATCAGGATTATCAACATTAGC |

The 50 µL of PCR mixture contained 1×GDP-HiFi PCR buffer B, 200 µM of mixture of dATP, dTTP, dGTP, and dCTP, 1 µM of amplification primer, 100 ng of pJET-P46 and 1 U GDP-HiFi DNA polymerase. The PCR reaction conditions were: 98° C. for 2 minutes (one cycle); 94° C. for 30 seconds, 55° C. for 30 seconds, 68° C. for 45 seconds (35 cycles); 68° C. for 5 minutes (one cycle). After the PCR reaction, gel electrophoresis was conducted to confirm the existing of the amplified DNA fragment of expected size.

The PCR products were collected by using Gel-M™ gel extraction system kit and the experiments were conducted according to the manual. Then, the four PCR products collected were used as the templates for gene amplification with P46F/P46R primer set. The PCR reaction conditions were: 98° C. for 2 minutes (one cycle); 94° C. for 30 seconds, 55° C. for 30 seconds, 68° C. for 45 seconds (35 cycles); 68° C. for 5 minutes (one cycle). After that, the whole length of the P46 gene being point mutated can be obtained. The PCR products were collected by using PCR-M™ Clean Up System Kit (GeneMark, Taiwan). And the cloning of the mutation gene was made by using CloneJET PCR Cloning Kit. For those transformation strains being confirmed, by colony PCR, successfully had insert DNA in their recombinant plasmids, the plasmids were extracted for DNA sequencing. The plasmid having the mutated P46 gene was named as pJET-P46M.

Example 4: Establishment of the Present *M. hyopneumoniae* Antigen Expression Vector Plasmids having various fusion partners were used as backbone for establishing *M. hyopneumoniae* antigen expression vector. The fusion partner genes used were MsyB of *E. coli*, YjgD of *E. coli*, the partial peptide of GroS containing 17 amino acids (GroS17) of *E. coli*, GroES of *Bacillus subtilis*, TrxA of *Alicyclobacillus acidocaldarius*, SUMO of *S. cerevisiae*, D protein of bacteriophage phiX174, and Vgb of *Vitreoscilla* spp. The establishment was made as follows:

1. The Establishment of MHP30 Expression Vector.

Cutting pJET-MHP30 with BamHI and SalI and the resulted DNA fragment was ligased into a fusion expression plasmid pre-cut by the same restriction enzymes. The ligation product was than transformed into *E. coli* ECOS 9-5. Transformation strains were screened by colony PCR and confirming if there was DNA fragments of expected size by using DNA electrophoresis. For those transformation strains being confirmed successfully had insert DNA in their recombinant plasmids, the plasmids were extracted out for DNA sequencing. The plasmids having correct DNA sequence were respectively named as pET-MSY-MHP30, pET-YjgD-MHP30, pET-GroS17-MHP30, pET-GroES-MHP30, pET-TrxA-MHP30, pET-SUMO-MHP30, pET-D-MHP30, and pET-Vgb-MHP30.

2. The Establishment of P46 Expression Vector.

Cutting pJET-P46M with BamHI and SalI and the following experiments were conducted by referring to the aforesaid establishment steps of MHP30 expression vector. The plasmids having correct DNA sequence were respectively named as pET-D-P46M, and pET-MSY-P46M.

3. The Establishment of NrdFC Expression Vector.

Cutting pJET-NrdFC with BamHI and SalI and the following experiments were conducted by referring to the aforesaid establishment steps of MHP30 expression vector. The plasmids having correct DNA sequence were respectively named as pET-D-NrdFC, and pET-MSY-NrdFC.

4. The Establishment of Tuf Expression Vector.

Cutting pJET-Tuf with BamHI and SalI and the following experiments were conducted by referring to the aforesaid establishment steps of MHP30 expression vector. The plasmids having correct DNA sequence were respectively named as pET-D-Tuf, and pET-MSY-Tuf.

Example 5: Expression of Recombinant *M. hyopneumoniae* Antigens and Purification Thereof Regarding to Expression of the Desired Antigens The antigen expression vectors were transformed into *E. coli* BL21 (DE3). One single colony was picked and inoculate on LB medium containing kanamycin of final concentration of 30 μg/mL and cultured under conditions of 37° C. and 180 rpm overnight. Then the broth was inoculated into fresh LB medium (containing kanamycin of final concentration of 30 μg/mL) at a ratio of 1:100 and cultured conditions of 37° C. and 180 rpm until the $OD_{600}$ value thereof achieving around 0.6~0.8. 0.1 mM of IPTG was added in for inducing the expression of the desired protein for 4 hours. Then, the broth was put under centrifugation (10,000×g, 10 minutes, 4° C.) and the pellet was collected. After that, the soluble portion and the insoluble portion thereof were separated by using Easy-Lyse Bacterial Protein Extraction kit (Epicentre, USA). Protein electrophoresis was then conducted to observe the solubility of the produced recombinant antigens.

FIGS. 1 and 2 respectively showed different solubility of MHP30 upon using various fusion partners in expression; and different solubility of P46, NrdFC, and Tuf upon using various fusion partners in expression. The results indicated that using YjgD, SUMO, GroS17, GroES, Vgb, or TrxA as fusion partner can increase the solubility of MHP30. On the other hand, using MsyB as fusion partner can provide P46, NrdFC, and Tuf excellent solubility.

Regarding to Purification of the Desired Antigens

Taking the advantage of the fact that the N' Hig tag of recombinant protein can form coordinate covalent bond with nickel or cobalt ion, immobilized-metal affinity chromatography (IMAC) was used for protein purification. The protocol of protein purification was referred to The QIA Expressionist™ (fourth edition, Qiagen). The pellet was suspended in lysis buffer (50 mM $NaH_2PO_4$, 300 mM NaCl, 10 mM imidazole, pH 8.0) and broken by homogenizer. Then, centrifugation was conducted and the supernatant was collected. The collected supernatant was introduced into a resin column (1 mL Ni-NTA) where the recombinant antigen would attach on. After that, 15 mL of wash buffer (50 mM NaH2PO4, 300 mM NaCl, 20 mM imidazole, pH 8.0) was added in to wash the resin inside the column to remove non-specific binding of proteins. Lastly, 20 mL of elution buffer (50 mM $NaH_2PO_4$, 300 mM NaCl, 250 mM imidazole, pH 8.0) was introduced to elute the antigens on the resin. The elution buffer contained high concentration of imidazole to compete the binding site on the resin with the recombinant proteins so that the recombinant proteins can be washed off from the resin. The result of purification was observed by protein electrophoresis. According to FIG. 3, it clearly showed that the His tag tagged on N' of the present recombinant antigens was indeed favorable for purifying the present recombinant antigens by IMAC.

Example 6: Mice Antiserum Trials

This example used 5-week BALB/c female mice (National Laboratory Animal Center). The mice were maintained in standard animal room with air conditioner and offered with food and clean water. The immune challenge was conducted after the mice being raised 7 days. The recombinant antigens purified in the aforesaid examples was mixed with adjuvant as a mixture (complete Freund's adjuvant or incomplete Freund's adjuvant) through a three-way connector and subcutaneously injected into the mice. The first injection was a complete Freund's adjuvant formulation. After 7 days from the first injection, the mice were injected with incomplete Freund's adjuvant formulation twice in a 7 days interval. After 7 days from the second injection, blood was collected from eye orbit of the mice.

The collected blood samples were placed in room temperature for 1 hour and placed at 4° C. overnight to let the blood coagulate. Then, the samples were put under centrifugation (5,000×g) for 30 minute to obtain the antiserum, which contained specific antibody against the recombinant antigen.

The obtained antiserum was then used to against total cell lysate of *M. hyopneumoniae*. The experiment protocol was: suspending *M. hyopneumoniae* PRIT-5 in SET buffer (50 mM glucose, 25 mM-HCl, 10 mM EDTA, pH 8.0) and adding 5× sample buffer (312.5 mM Tris-HCl (pH 6.8), 50% glycerol, 10% SDS, 0.05% bromophenol blue); heating the sample at 100° C. for 5 minutes after the sample was well-mixed with the aforesaid buffer. Then, protein electrophoresis was conducted. The gel, after protein electrophoresis, was immersed in transfer buffer (25 mM Tris base, 192 mM glycine, 10% (v/v) methanol, pH 8.3). PVDF membrane of suitable size was rinsed with methanol for few seconds, washed by deionized water, and then immersed into transfer buffer. After the gel and PVDF membrane were both immersed in transfer buffer for 15 minutes, a filter paper, the gel, the PVDF membrane and another filter paper were sequentially placed in a Trans-Blot SD Semi-Dry Transfer Cell for transferring under suitable electric supply. After the transferring was done, the PVDF membrane was immersed in 20 mL of block buffer (20 mM Tris, 150 mM NaCl, 5% skim milk, pH7.4) in room temperature for 1 hour and 10 µL of recombinant antigen was added in (2000× diluation). After shaking in room temperature for 1 hour, the block buffer was discarded and the PVDF membrane was by 20 mL TBST buffer (20 mM Tris, 150 mM NaCl, 0.05% Tween-20, pH7.4) three times (5 minute for each time). 20 mL of block buffer and 4 µL of alkaline phosphatase-conjugated goat anti-mouse IgG (H+L) were then added in and the mixture was shaken in room temperature for 1 hour. After that, the PVDF membrane was washed by TBST buffer three times and NBT/BCIP reagent was added in for detection.

Figure 1:
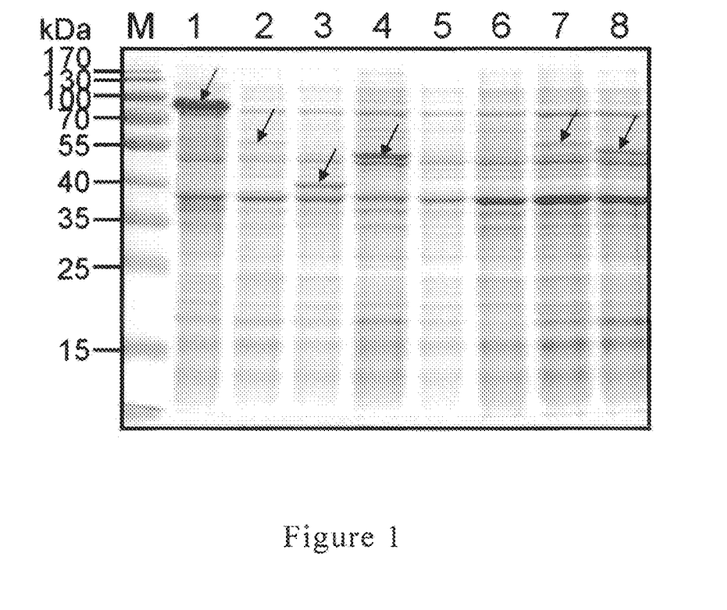
Figure 2:
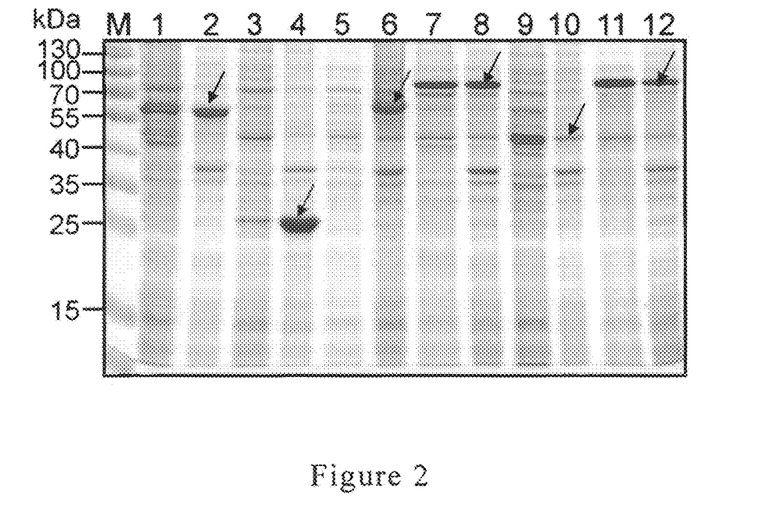
FIG. 2 is a result of a protein electrophoresis, showing various fusion partners have different effects on the solubility of P46, NrdFC, and Tuf prepared. Line M: protein marker (PageRuler™ pretained protein ladder; Fermentas, USA); Line 1: *E. coli* BL21 (DE3) (pET-D-P46M), soluble protein; Line 2: *E. coli* BL21 (DE3) (pET-D-P46M), insoluble protein; Line 3: *E. coli* BL21 (DE3) (pET-D-NrdFC), soluble protein; Line 4: *E. coli* BL21 (DE3) (pET-D-NrdFC), insoluble protein; Line 5: *E. coli* BL21 (DE3) (pET-D-Tuf), soluble protein; Line 6: *E. coli* BL21 (DE3) (pET-D-Tuf), insoluble protein; Line 7: *E. coli* BL21 (DE3) (pET-MysB-P46M), soluble protein; Line 8: *E. coli* BL21 (DE3) (pET-MysB-P46M), insoluble protein; Line 9: *E. coli* BL21 (DE3) (pET-MysB-NrdFC), soluble protein; Line 10: *E. coli* BL21 (DE3) (pET-MysB-NrdFC), insoluble protein; Line 11: *E. coli* BL21 (DE3) (pET-MysB-Tuf), soluble protein; Line 12: *E. coli* BL21 (DE3) (pET-MysB-Tuf), insoluble protein.
Figure 3:
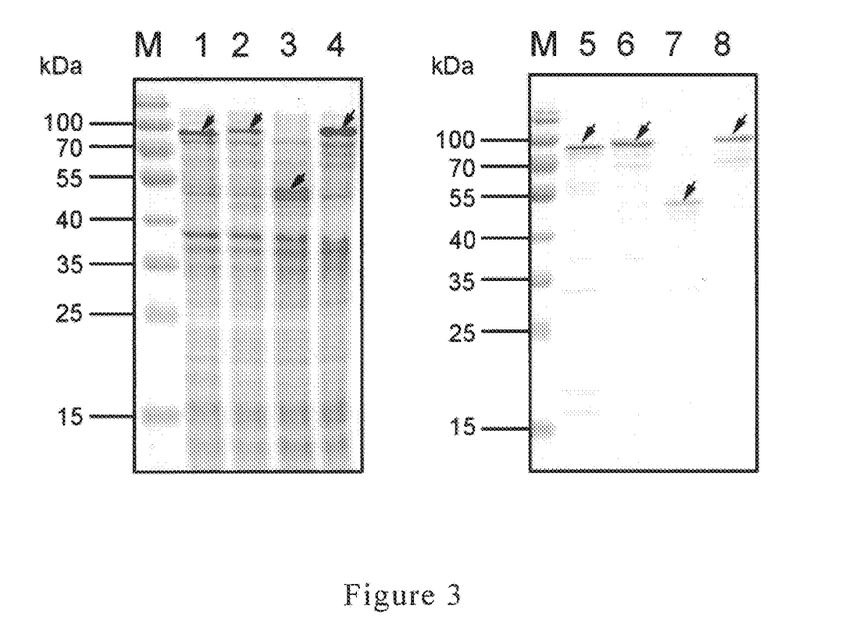
FIG. 3 is a result of a protein electrophoresis, showing the purification of the present recombinant proteins MHP30, P46, NrdFC, and Tuf. Line M: protein marker (PageRuler™ pretained protein ladder; Fermentas, USA); Line 1: *E. coli* BL21 (DE3) (pET-YjgD-MHP30), soluble protein; Line 2: *E. coli* BL21 (DE3) (pET-MysB-P46M), soluble protein; Line 3: *E. coli* BL21 (DE3) (pET-MysB-NrdFC), soluble protein; Line 4: *E. coli* BL21 (DE3) (pET-MysB-Tuf), soluble protein; Line 5: purified MHP30 fusion protein; Line 6: purified P46 fusion protein; Line 7: purified NrdFC fusion protein; Line 8: purified Tuf fusion protein.
Figure 4:
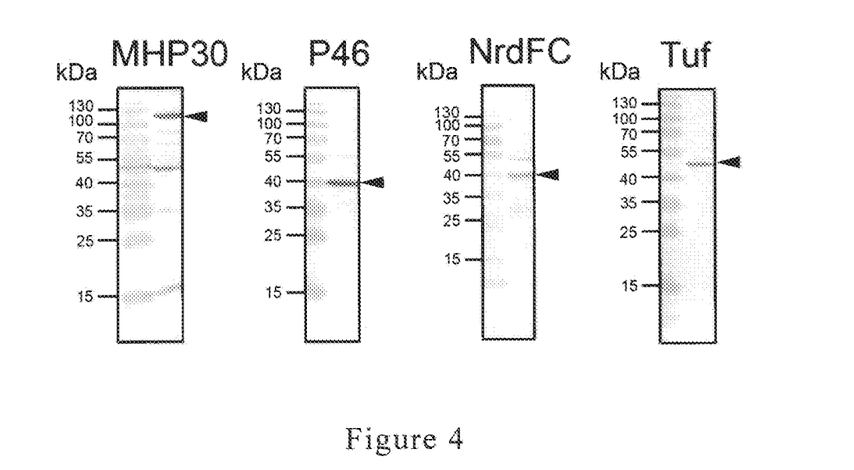
FIG. 4 shows the result of Western Blot assay, showing that mice antiserum identified the total cell lysate of *M. hyopneumoniae*.

The result showed that the mixture of the present recombinant antigen and suitable adjuvant did induce antibody against the antigen in mice. That is to said, the present proteins had potential to be immunogens (FIG. 4).

Example 7: Swine Immune Tests and Challenge Tests

1. Vaccine Preparation.

One or more of the purified recombinant antigens of the aforesaid examples were mixed with an adjuvant to obtain desired subunit vaccines or cocktail vaccines. The dosage of every vaccine prepared was 2 mL, which contained 200 µg of each kind of the present proteins added.

2. Swine Immune Tests.

The aforesaid subunit vaccines or cocktail vaccines were used for swine immune tests. 2-weeks SPF swine were bought from the second generation SPF swine house of Animal Technology Institute Taiwan. All the swine were maintained and fed equally in the SPF swine house.

Figure 5:
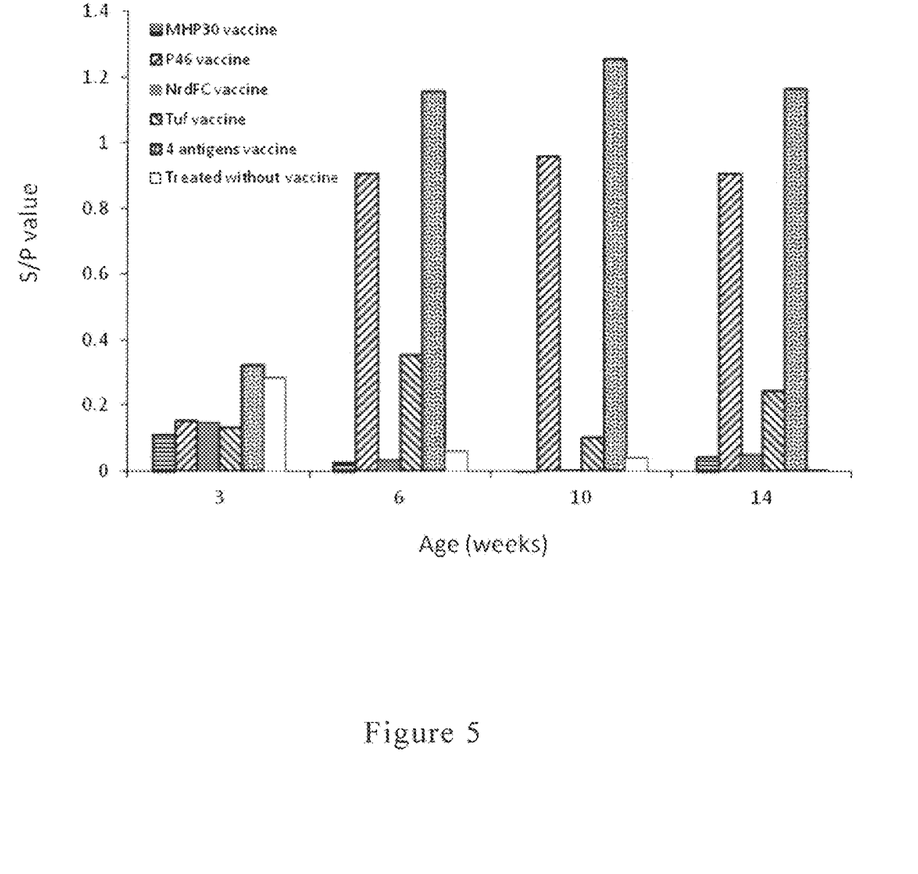
FIG. 5 shows the result of ELISA assay, showing the results of the immune challenge experiments conducted in Embodiment 7 of the present invention.

The vaccines (2 mL) were intramuscularly injected to the swine when they reached 21-day age and blood thereof was collected at 21, 42, 70, and 98-day age for isolating serum. *Mycoplasma* spp. antibody trials (IDEXX) kit was used for analyzing the collected serum antibodies. The operation was as the follows. First of all, 10 µL of serum was mixed with 390 µL of sample diluents gently to obtain a mixture. 100 µL of the mixture was added in the wells of a 96-well plate, which already had *Mycoplasma* spp. antigen inside. Besides, 100 µL of positive serum and negative serum were also added to different wells of the plate as controls. The plate was placed in room temperature for 30 minutes. Then, the liquid in the plate was discarded and 350 µL of wash buffer was added in three times for washing. 350 µL of horseradish peroxidase labeled with anti-swine antibodies was then added in to the plate and the plate was placed in room temperature for 30 minutes. After that, the liquid in the plate was discarded and 350 µL of wash buffer was added in three times for washing. 100 µL of TMB substrate solution was added into the plate and the plate was placed in room temperature for 15 minutes. Then, 100 µL of stop buffer was added to terminate the color reaction. Lastly, the absorbance of each well was evaluated at 650 nm by an ELISA reader for calculation of S/P value. S/P value=($OD_{650}$ absorbance of trial group–$OD_{650}$ absorbance of negative control group)/($OD_{650}$ absorbance of positive control group–$OD_{650}$ absorbance of negative control group). The higher the S/P value, the more the antibodies against *M. hyopneumoniae* proteins. The experiment results showed that the present antigens were able to induct immune response; wherein P46 vaccine and cocktail vaccine (contained the four antigens in one vaccine: P46, Tuf, MHP30, and NrdFC) showed the best induction effect and the induced immune response can be maintained until 14-week age (FIG. 5).

3. Swine Challenge Tests.

Bayovac® MH-PRIT-5 vaccine prepared by using *M. hyopneumoniae* PRIT-5 was used in this experiment as control for evaluating the immune efficacy of the present subunit vaccine and cocktail vaccine. 4-weeks SPF swine were bought from the second generation SPF swine house of Animal Technology Institute Taiwan. All the swine were maintained and fed equally in the SPF swine house.

The *M. hyopneumoniae* bacterial broth used for the challenge tests was prepared by: a swine lung tissue (about 3×3 $cm^2$) infected by *M. hyopneumoniae* was collected and ground in 20 mL of Friis medium. After centrifugation (148.8×g) for 10 minutes, the supernatant was transferred to a clean tube for centrifugation (7,870×g) for another 40 minutes. Then, the supernatant was discarded and the precipitation was re-suspended with 6 mL of Friis medium to obtain a suspension. After that, the suspension was filtered sequentially by 5 µm and 0.45 µm filters to obtain the challenge bacterial broth needed for this experiment.

The vaccines (2 mL) were intramuscularly injected to the swine when they reached 35-day age. Another injection was made at 49-day age via the same way. At 63-day age, the immuned swine were anesthetized and challenged by administering the challenge bacterial broth (5 mL) via trachea. After 28 days from the day being challenged, the swine were scarified and the lungs thereof were collected for evaluating the immune effect. The evaluation of the immune effect was made according to the following criteria: any one of meddle upper lobes and upper lobes of any side of the lung observed of pathological trait was scored as 10 points; any of meddle upper lobe and diaphragmatic lobes of any side of the lung observed of pathological trait was scored as 5 points. The full score was 55 points. The observation records were shown in Table 4.

TABLE 4

Evaluation of lung lesion in the challenge tests

| Antigen(s) | Point of lung lesion |
| --- | --- |
| MHP30 | 27 |
| P46 | 25 |
| NrdFC | 26 |

TABLE 4-continued

Evaluation of lung lesion in the challenge tests

| Antigen(s) | Point of lung lesion |
|---|---|
| Tuf | 23 |
| MHP30 + NrdFC + P46 + Tuf | 17 |
| PRIT-5 vaccine (positive control) | 23 |
| No vaccine used (negative control) | 30 |

According to the data shown in Table 4, it is clear that the subunit vaccines of the present invention were able to provide equivalent immune effects as conventional vaccine (Bayovac® MH-PRIT-5). Furthermore, the cocktail vaccine (contained the four antigens in one vaccine: P46, Tuf, MHP30, and NrdFC) exhibited better immune effect significantly than the conventional vaccine. To sum up, the present proteins indeed are suitable to be applied as active ingredients of vaccines and those proteins exhibited synergistic effect while being used in combination as cocktail vaccine.

Those having ordinary skill in the art can readily understand any possible modifications based on the disclosure of the present invention is without apart from the spirit of the present invention. Therefore, the examples above shall not be used for limiting the present invention but intend to cover any possible modifications under the spirit and scope of the present invention according to the claims recited hereinafter.

What is claimed is:

1. A composition, comprising:
   an active ingredient, comprising P46; wherein said P46 comprises SEQ ID NO: 01; and
   an immune-effective amount of a pharmaceutically acceptable adjuvant.

2. The composition of claim 1, said active ingredient further comprises a protein selected from a group consisting of MHP30, NrdFC, and a combination thereof; wherein said MHP30 comprises SEQ ID NO: 03; and said NrdFC comprises SEQ ID NO: 04.

3. The composition of claim 2, wherein each active ingredient protein is independently present at a concentration of 20 to 2000 µg/mL based on the total volume of said composition.

4. The composition of claim 1, wherein said pharmaceutically acceptable adjuvant is a complete Freund's adjuvant, an incomplete Freund's adjuvant, an alumina gel, a surfactant, a polyanion adjuvant, a peptide, an oil emulsion, or a combination thereof.

5. The composition of claim 1, further comprising a pharmaceutically acceptable additive.

6. The composition of claim 5, wherein said pharmaceutically acceptable additive is a solvent, a stabilizer, a diluent, a preservative, an antibacterial agent, an antifungal agent, an isotonic agent, an absorption delaying agent, or a combination thereof.

* * * * *